United States Patent
Kerrigan et al.

(10) Patent No.: US 10,440,930 B1
(45) Date of Patent: Oct. 15, 2019

(54) HYBRID MUSHROOM STRAIN J15987 AND DERIVATIVES THEREOF

(71) Applicant: SYLVAN AMERICA, INC., Kittanning, PA (US)

(72) Inventors: Richard W. Kerrigan, Kittanning, PA (US); Mark P. Wach, Allison Park, PA (US); Michael A. Kessler, Kittanning, PA (US); Mark G. Loftus, Oakmont, PA (US); Michelle E. Schultz, New Bethlehem, PA (US); William P. Swanik, Petrolia, PA (US); Anthony J. Velko, Jr., Ford City, PA (US)

(73) Assignee: SYLVAN AMERICA, INC., Kittanning, PA (US)

( * ) Notice: Subject to any disclaimer, the term of this patent is extended or adjusted under 35 U.S.C. 154(b) by 0 days.

(21) Appl. No.: 16/045,079

(22) Filed: Jul. 25, 2018

(51) Int. Cl.
*A01H 15/00* (2006.01)

(52) U.S. Cl.
CPC .................................... *A01H 15/00* (2013.01)

(58) Field of Classification Search
CPC ...................................................... A01H 15/00
See application file for complete search history.

(56) References Cited

U.S. PATENT DOCUMENTS

| | | | |
|---|---|---|---|
| 7,608,760 B2 | 10/2009 | Robles et al. | |
| 9,017,988 B1 | 4/2015 | Kerrigan et al. | |
| 9,622,428 B2 * | 4/2017 | Kerrigan | A01H 15/00 |
| 9,642,333 B2 | 5/2017 | Kerrigan et al. | |
| 9,648,812 B2 | 5/2017 | Kerrigan et al. | |
| 2010/0212042 A1 | 8/2010 | Robles et al. | |

FOREIGN PATENT DOCUMENTS

WO  2015127210 A1  8/2015

OTHER PUBLICATIONS

D.M. Beyer; Department of Plant Pathology, The Pennsylvania State University. Plant Disease—97 (1):142—Abstract; apsjournals.apsnet.org/doi/abs/10.1094/PDIS-07-12-0619-PDN; Jan. 2013, vol. 97, No. 1p. 142; 2 pages.

Xu, J.-P., et al. 1993. Localization of the mating type gene in Agaricus bisporus. App. Env. Microbiol. 59(9): 3044-3049.

Emmanuelle Morin, et al.; Environmental Sciences; www.pnas.org; 4146-4148, PNAS, Mar. 5, 2013, vol. 110, No. 10; 9 pages.

A.J. Velcko, Jr. et al.; Expression of Novel Genes in Agaricus Bisporus Using an Agrobacterium-mediated Transformation Technique; 4 pages in Science and Cultivation of Edible and Medicinal.

Micheline Imbernon, et al.; MYCOLOGIA; 88(5), 1996, pp. 749-761; BSN, the Primary Determinant of basidial spore number and reproductive mode in Agaricus bisporus, maps to chromosome I; 13 pages.

Callac, P., et a., 1998. Evidence for PPC1, a determinant of the pilei-pellis color of Agaricus bisporus fruitbodies. Fungal Genet. Biol. 23, 181-188.

Foulongne-Oriol, et al., 2010. An expanded genetic linkage map of an intervarietal *Agaricus bisporus* var. bisporus.—A. bisporus var. burnettii hybrid based on AFLP, SSR and CAPS markers sheds light on the recombination behaviour of the species. Fungal Genetics and Biology 47: 226-236.

Kerrigan, R.W., et al., 1993.Meiotic behavior and linkage relationships in the secondarily homothallic fungus Agaricus bisporus. Genetics 133, 225-236.

Loftus, M., et al., 2000. Use of SCAR marker for cap color in Agaricus bisporus breeding programs. Mush. Sci. 15, 201-205.

Schoch, Conrad L., et al., 2012. Nuclear ribosomal internal transcribed spacer (ITS) region as a universal DNA barcode marker for Fungi. Proc. Nat. Acad. Sci.

* cited by examiner

*Primary Examiner* — David H Kruse

(74) *Attorney, Agent, or Firm* — Renner Kenner Greive Bobak Taylor & Weber

(57) ABSTRACT

A hybrid mushroom culture of *Agaricus bisporus*, designated as strain J15987, includes a representative culture of the strain, which has been deposited under NRRL Accession No. 67646.

2 Claims, No Drawings

HYBRID MUSHROOM STRAIN J15987 AND DERIVATIVES THEREOF

TECHNICAL FIELD

This invention relates to a novel hybrid culture of the edible, cultivated mushroom fungus *Agaricus bisporus* (Lange) Imbach, and related Essentially Derived Varieties thereof. More particularly, this invention relates to a newly developed hybrid strain designated J15987 and to cultures that are descended, or otherwise derived, from *Agaricus bisporus* strain J15987, including Essentially Derived Varieties.

BACKGROUND OF THE INVENTION

The edible mushroom *Agaricus bisporus* (Lange) Imbach var. *bisporus*, a microorganism belonging to the basidiomycete fungi, is widely cultivated around the world. In Europe and North America, it is the most widely cultivated mushroom species. The value of the annual *Agaricus bisporus* mushroom crop in the United States was about $1,110,000,000 in 2012-2013, according to the National Agricultural Statistics Service, Agricultural Statistics Board, U.S. Department of Agriculture (Aug. 20, 2013).

Cultures of *Agaricus*, like those of other microorganisms, are prepared, maintained, propagated and stored on sterile media using microbiological laboratory methods. Sterile tools and aseptic techniques are used within clean rooms or sterile transfer hoods to manipulate cells of the pure cultures for various purposes including clonal propagation and for the development of new strains using diverse techniques including spore germinations on sterile growth media and controlled matings on sterile growth media. Commercial culture inocula including mushroom 'spawn' and 'casing inoculum' are also prepared using large-scale microbiological production methods, for example by aseptically introducing inoculum of a pure culture of a strain of *Agaricus bisporus* into from one to 14,000 liters of sterilized growth media under sterile conditions, and are provided to the end user as pure cultures on sterile growth media contained within sterile packaging.

Mushrooms are cultivated commercially within purpose-built structures on dedicated farms. While there are many variations on methods, the following description is typical. Compost prepared from lignocellulosic material such as straw, augmented with nitrogenous material, is finished and pasteurized within a suitable facility. Mushroom spawn, which comprises a sterilized friable 'carrier substrate' onto which a pure culture of one mushroom strain has been aseptically incorporated via inoculum and then propagated, is mixed with the pasteurized compost and is incubated for approximately 13 to about 19 days at a controlled temperature, during which time the mycelium of the mushroom culture colonizes the entire mass of compost and begins to digest it. A non-nutritive 'casing layer' of material such as peat is then placed over the compost to a depth of from about 1.5 to about 2 inches. Additional 'casing inoculum' incorporating the same mushroom culture may be incorporated into the casing layer to accelerate the formation and harvesting of mushrooms, and improve uniformity of the distribution of mycelium and mushrooms in and on the casing surface. Environmental conditions, including temperature and humidity, in the cropping facility are then carefully managed to promote and control the transition of the culture from vegetative to reproductive growth at the casing/air interface. In a further about 13 to about 18 days after casing, mushrooms will have developed to the correct stage for harvest and sale. A flush of mushrooms comprising the original culture will be picked over a 3 to 4 day period. Additional flushes of mushrooms appear at about weekly intervals. Commercially, two or three flushes of mushrooms are produced and harvested before the compost is removed and replaced in the cropping facility.

Seventy to ninety-five percent of the *Agaricus* mushrooms cultivated in the United States, Europe, and elsewhere have a white pileus color, in accordance with consumer preferences. Market requirements for white mushrooms in the USA and elsewhere are narrow and precise for many observable phenotypic traits such as size, shape, color, color retention, firmness, and related traits such as shelf life. Consequently, genetically different strains of commercially successful white *Agaricus bisporus* mushrooms are not easily differentiated on the basis of appearance of the mushrooms, which must conform to the relatively strict market requirements. Strains may, to some extent, be differentiated on the basis of traits associated with the mushroom, such as mushroom size, mushroom shape (e.g., cap roundness, flesh thickness), color (i.e., white cap versus brown cap), surface texture (e.g., cap smoothness), tissue density and/or firmness, delayed maturation, basidial spore number greater than two, sporelessness, increased dry matter content, improved shelf life, and reduced bruising, as well as traits associated with the culture itself, and/or products incorporating the culture, and/or crops incorporating the culture, including increased crop yield, altered distribution of yield over time, decreased spawn to pick interval, resistance to infection by, symptoms of, or transmission of bacterial, viral or fungal diseases, insect resistance, nematode resistance, ease of crop management, suitability of crop for mechanical harvesting, and behavioral responses to environmental conditions including stressors, nutrient substrate composition, seasonal influences, farm practices, self/non-self interactions (compatibility or incompatibility) with various mushroom strains, to give some examples. Strains may also be differentiated based on their genotypic fingerprint (presence of specific alleles at defined marker loci in the nuclear or mitochondrial genome). Strains may have different ancestry, which will be reflected directly by the genotype, and indirectly, in some cases, by the phenotype.

Circa 1980, the first two white hybrid strains of *A. bisporus*, developed by a laboratory at Horst, the Netherlands, were introduced into commercial cultivation. These two "Horst" strains, called U1 and U3, are closely related hybrid strains produced by matings between two pre-existing white cultivated strains, as per M. Imbernon et al., *Mycologia*, 88(5), 749-761 (1996), herein incorporated by reference. The two parents of U1 and U3 are commercial strains belonging to two longstanding categorical types of strains known as the 'smooth-white' (SW) strains and the 'off-white' (OW) strains. The original homokaryons (or 'lines') obtained from the SW and OW strains, and used in the hybridization that produced the U1 strain, were designated H39 and H97 respectively; these cultures may no longer exist (A. Sonnenberg, pers. comm.). However, a number of laboratories have deheterokaryotized the U1 strain and obtained neohaplont cultures incorporating one or the other nuclear type corresponding to those contributed by H39 or H97, as well as the mitochondrial type of U1. We refer to these two types of neohaplonts of U1 categorically as the SWNC and OWNC lines or homokaryons, respectively. An OWNC line designated 'H97' was deposited in the public culture collection of the Fungal Genetics Stock Center of Kansas, USA, by A. Sonnenberg, under the number 10389, and in the public collection of the American Type Culture Collection of Maryland, USA, under the number MYA-4626. The genome of H97 was sequenced and placed in the public domain by the Joint Genome Institute of California, USA (Morin et al. 2012, herein incorporated by reference).

The U1 strain is thought to be the direct progenitor of all other white *A. bisporus* mushrooms currently cultivated in most regions of the world. Many commercial mushroom strains developed from U1 such as A-15 and S130 meet the criteria for Essentially Derived Varieties (as the term is applied to plant varieties, e.g. in the Plant Variety Protection Act) of U1, having been developed from spores of the initial strain which retain the great majority of the parental genotype (this behavior was shown by R. W. Kerrigan et al. in *Genetics*, 133, 225-236 (1993), herein incorporated by reference). A group of strains developed either by cloning or by spore culture, or by any other method of 'essential derivation' as discussed below, from a single progenitor (as opposed to outbreeding between two different progenitors) is called a derived lineage group. Except for relatively minor acquired genetic differences all white strains developed within the Horst U1 derived lineage group share a single composite N+N heterokaryotic genotype, or a subset of that genotype, with the original U1 strain. For this reason, modern white *Agaricus* mushroom cultivation is effectively a monoculture.

*Agaricus bisporus* has a reproductive syndrome known as amphithallism, in which two distinct life cycles operate concurrently. As in other fungi, the reproductive propagule is a spore. *Agaricus* produces spores meiotically, on a meiosporangium known as a basidium. In a first life cycle, *A. bisporus* spores each receive a single haploid postmeiotic nucleus; these spores are competent to mate but not competent to produce mushrooms. These haploid spores germinate to produce homokaryotic offspring or lines which can mate with other compatible homokaryons to produce novel hybrid heterokaryons that are competent to produce mushrooms. Heterokaryons generally exhibit much less ability to mate than do homokaryons. This life cycle is called heteromixis, or more commonly, outbreeding. This life cycle operates but typically does not predominate in strains of *Agaricus bisporus* var. *bisporus*.

A second, inbreeding life cycle called intramixis predominates in most strains of *Agaricus bisporus* var. *bisporus*. Most spores receive two post-meiotic nuclei, and most such pairs of nuclei consist of Non-Sister Nuclear Pairs (NSNPs) which have a heteroallelic genotype at most or all centromeric-linked loci including the MAT locus. That MAT genotype determines the heterokaryotic phenotype of these offspring, which are reproductively competent and can produce a crop of mushrooms. Unusually among eukaryotes, relatively little chromosomal crossing-over is observed to have occurred in postmeiotic offspring of *A. bisporus*; empirically, very little heteroallelism (analogous to heterozygosity) is lost among heterokaryotic offspring of a heterokaryotic strain. Consequently, parental and offspring heterokaryotic genotypes and phenotypes tend to closely resemble each other, as noted above; for this reason, essential derivation, e.g., the production of Essentially Derived Varieties (EDVs), is a familiar strain development technique among commercial mushroom spawn producers.

There is a need for commercially acceptable *A. bisporus* strains with different genotypes, relative to the U1 derived lineage group, for two reasons. First, strains incompatible with strains of the U1 derived lineage group are known to retard the spread of viral diseases between strains, which diseases are known problems in the commercial mushroom industry. Second, it is well understood that when an agricultural crop industry relies extensively on a single genetic lineage (i.e., creates a commercial monoculture as now exists for the white-capped U1 lineage-group of *A. bisporus*), there is an increased risk of unpredictable, catastrophic crop failure on a facility-wide or industry-wide scale. Therefore from a risk management and food security perspective, it is highly desirable to simultaneously provide both genetic diversification and commercially acceptable performance and crop characteristics.

SUMMARY OF THE INVENTION

The present invention is generally directed to a new and distinct *Agaricus bisporus* mushroom culture comprising the newly developed hybrid strain J15987 or Essentially Derived Varieties (EDVs) of strain J15987, which in general are functionally equivalent to the J15987 strain. A deposit of a culture of hybrid strain J15987, as disclosed herein, has been made with the Agricultural Research Services Culture Collection (NRRL) 1815 North University Street, Peoria, Ill. 61604 USA. The date of deposit was Jul. 23, 2018. The culture deposited was taken from the same culture maintained by Sylvan America, Inc., Kittanning, Pa., the assignee and applicant of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 676464. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the filing the priority application or upon the issuance of a patent on this strain according to the patent laws.

Such cultures of strain J15987 and of EDVs of J15987 are noted to produce mushrooms, parts of mushrooms, parts of the culture, and strains and lines descended or derived from such cultures. Thus, the present invention encompasses strain J15987, Essentially Derived Varieties of strain J15987, dormant or active growing cultures present in dormant or germinating spores of strain J15987, and cultures incorporating the genetic material of strain J15987. The present invention is also directed towards methods of making and using strain J15987.

With respect to spores, living spores are heterokaryons or homokaryons in a dormant state. Spores are one part of the mushroom organism. Other parts include caps, stems, gills, cells (defined as hyphal compartments incorporating nuclei, mitochondria, cytoplasm, protoplasts, RNA, DNA, proteins, cell membranes, and cell walls including crosswalls), hyphae, and mycelium. Spores may be aseptically collected on sterile material, suspended in sterile water at various dilutions, and plated onto sterile agar growth media in order to produce germinated spores and the cultures incorporated within the spores. A preferred technique is to have within the enclosed petri plate a living *Agaricus* culture which may stimulate spore germination via the diffusion of a volatile pheromone. Germinated spores may be isolated under a microscope using sterile microtools such as steel needles, onto fresh nutrient agar plates. Using this method, heterokaryotic and homokaryotic offspring of strain J15987 comprising the spores and the cultures incorporated within the spores of strain J15987 may be obtained.

Development of novel hybrid varieties via heteromixis comprises the controlled physical association and mating of two compatible cultures to obtain a novel heterokaryon culture. Homokaryons (='lines') are the preferred starting cultures for making matings as they have maximal ability to anastomose and achieve plasmogamy with other cultures. Heterokaryons may also be placed in physical contact but with commercially unreasonably low probabilities of a mating resulting in successful formation of a novel heterokaryon. Compatibility is determined by the genotype at the MAT locus; two homokaryons with the same MAT allele cannot establish a heterokaryon after anastomosis. In a defined mating program, homokaryotic lines are obtained and are associated in predetermined pairwise combinations. In one method, homokaryon pairs may be placed in close proximity on the surface of a nutrient agar medium in a petri dish and allowed to grow together (in a physical association), at which point anastomoses between the two cultures occur. A successful outcome is a mating. The novel hybrid heterokaryon may be obtained by transferring mycelium from the fusion zone of the dish. Such a paired mating method, between homokaryotic line J11500-s80 and line s-290, was used to develop the strain J15987.

In contrast, EDVs are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006). The definition employed herein is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples. DNA-mediated transformation of *A. bisporus* has been reported by Velcko, A. J. Jr., Kerrigan, R. W., MacDonald, L. A., Wach, M. P., Schlagnhaufer, C., and Romaine, C. P. 2004, Expression of novel genes in *Agaricus bisporus* using an *Agrobacterium*-mediated transformation technique. Mush. Sci. 16: 591-597, and references therein, herein incorporated by reference. Transformation may introduce a single new gene or allele into the genome of an initial culture.

EDVs are unambiguously recognizable by their genotype, which will be predominantly a subset of the single initial culture. Percentages of the initial genotype that will be present in *Agaricus bisporus* EDVs range from almost 100% in the case of somatic selections, to 99.x % in the case of strains modified by DNA-mediated transformation, to 90-99.x % in the case of single or multiple spore selections or some mutagenesis, to an average of 75-85% in the case of sibling-offspring matings (=selfing). Many methods of genotype determination, including methods described below, and others well known in the art, may be employed to determine the percentage of DNA of an initial culture that is present in another culture.

Repeated mating back to the initial culture to introgress a single trait into the genetic background of an initial culture is called introgressive trait conversion, and according to accepted definitions of EDVs, also produces an EDV of the initial culture. In a hypothetical example, in the first successive repetition of this process a resultant strain of this generation will have on average about 75% of the DNA of the initial strain while about 25% of the DNA will have been contributed by a second strain or line; as this process is repeated the DNA representation of the initial strain will increase, approaching 97% on average after 3 further successive repetitions. There is no universally accepted quantitative threshold for the proportion of DNA contributed by an initial culture in an EDV of an initial culture; we regard 75-100% genotype identity with an initial culture as indicative of an EDV of an initial culture. It is also established that an EDV of an EDV is also an EDV of an initial strain. Finally, because *Agaricus bisporus* alternates generations between heterokaryotic strains and homokaryotic lines, the criteria for essential derivation apply equally to cultures of both strains and lines. EDVs are, generally speaking, minor variants of the original strain or line, and have been accorded intellectual property rights co-extensive with those of the original strain or line.

Genotypic fingerprints are descriptions of the genotype at defined loci, where the presence of characterized alleles is recorded. Such fingerprints provide powerful and effective techniques for recognizing clones and all types of EDVs of an initial strain, as well as for recognizing ancestry within outbred lineages. Many techniques are available for defining and characterizing loci and alleles in the genotype. The most detailed approach is provided by whole-genome sequencing (WGS), which allows for direct characterization and comparison of DNA sequences across the entire genome. Using this approach to generate robust genotypic fingerprints incorporating large numbers of marker loci, it is possible to establish the nature of the relationship between two strains, including strains related by genealogical descent over several generations. Sylvan America, Inc., the inventor's assignee, has tracked genetic markers through four to six generations of its breeding pedigrees. If a sufficient number of rare markers are present in an initial strain or line, it will be possible to identify descent from an initial strain or line after several outbred generations without undue experimentation. In a hypothetical example, the mean expectation for genomic representation of an initial haploid line after 4 outbred generations is 3.1% ($50\%/2^4$) in an F4 hybrid, which corresponds to ca. 1 Mb of the nuclear genomic DNA of *A. bisporus*. Based on Sylvan America, Inc.'s analyses, that amount of DNA from each of two unrelated strains of *A. bisporus* may typically contain from about 10,000 to about 20,000 single nucleotide polymorphisms (SNPs), any one of which may provide a distinguishing marker linking the F4 hybrid to the initial line. By using multiple independent markers, ancestors of a strain can be identified with a very high probability of success and with reasonable confidence.

One trait of biological and commercial interest is heterokaryon incompatibility. The genetics of these self/non-self recognition systems are not well elucidated in basidiomycete fungi such as *Agaricus* but are known in other Fungal genera to involve multiple alleles at multiple independent loci. Differences in the presumed genotype at the incompatibility loci prevent successful anastomoses and cytoplasmic continuity among physical mixtures of two or more heterokaryons. One consequence of such antagonistic responses is a retardation of growth and development, and a reduction of crop yield; this sort of partial crop failure is well known and evident to the experienced grower. Another consequence of heterokaryon incompatibility is restriction on the opportunity for endocellular viruses to move freely throughout or among mycelial networks. Virus diseases such as those caused by the LIV or MVX viruses can have severe negative impacts on facility productivity and must be remediated using hygiene practices which can be assisted by strain rotation. A method of improving mushroom farm hygiene called 'virus-breaking' is carried out by replacing cropping material (compost, spawn, casing inoculum) incorporating an initial strain with inoculum and cropping material incorporating another different strain that is incompatible with the initial strain. In the most effective implementation of the virus-breaking method, all biological material of the initial strain at a mushroom farm is replaced with biological material of the second, incompatible strain. Strain incompatibility creates an effective if not absolute barrier to movement of virus from biological reservoirs within a facility into new crops. Rotating cultivation usage among mushroom strains of different genotypes may also interrupt infection and infestation cycles of exogenous pests and pathogens.

As noted above, hybrid mushroom strain producers are always looking for hybrid strains that allow growers to produce crops of mushrooms successfully and profitably. In the case of strain J15987 and strains derived or descended from that strain, positive attributes documented thus far include an attractive appearance (round cap shape, thick cap flesh, thick stem, less red cap surface color, compared to the widely used existing commercial strain A-15, all of which appeal to consumers) and a total harvested yield that may exceed that of strains like A-15. A mushroom grower can obtain a highly yielding crop of white-capped mushrooms with an attractive appearance and proportions by using strain J15987.

In addition, strain J15987 has a different genotype from the U1 derived lineage group. Accordingly, strain J15987 is incompatible with strains of the U1 derived lineage group, which is a characteristic known to retard the spread of viral diseases between strains, a known problem at commercial mushroom farms. Thus, strain J15987 confers a potential benefit in strain rotation programs designed to manage facility hygiene. Strain J15987 has been found to simultaneously provide both genetic diversification and commercially acceptable performance and crop characteristics.

These and other advantages of the present invention over existing prior art relating to *Agaricus bisporus* mushrooms and cultures, which shall become apparent from the description which follows, are accomplished by the invention as hereinafter described and claimed.

One or more aspects of the present invention may be accomplished by a hybrid mushroom culture of *Agaricus bisporus* designated as strain J15987, a representative culture of the strain having been deposited under NRRL Accession No. 67646. The strain J15987 may include various parts of the culture, including hyphae, spores, and cells and parts of cells, including, nuclei, mitochondria, cytoplasm, protoplasts, DNA, RNA, proteins, cell membranes and cell walls, said parts being present in both the vegetative mycelium of the culture and in mushrooms produced by the culture. The spores may be dormant or germinated spores, and may include heterokaryons and homokaryons incorporated therein.

One or more products incorporating the hybrid mushroom culture of *Agaricus bisporus* designated as strain J15987 may be produced. Such products include mycelium, spawn, inoculum, casing inoculum, fresh mushrooms, processed mushrooms, mushroom extracts and fractions, mushroom pieces, and colonized substrates selected from grain, compost, and friable particulate matter. It will be appreciated that mushroom pieces refer to stems, pilei, and other larger portions of the mushroom itself. Spores of the mushrooms may be dormant spores or germinated spores, and may include heterokaryons and homokaryons incorporated therein.

One or more other aspects of the present invention may be accomplished by an Essentially Derived Variety of the hybrid mushroom culture of strain J15987. In one or more embodiments, an *Agaricus bisporus* culture produced by essential derivation has at least one of the essential characteristics of strain J15987, for example the same heterokaryon compatibility phenotype, and/or the further characteristics of cap roundness, flesh thickness, yield performance, and yield timing relative to commercial strain A-15, wherein a culture of strain J15987 has been deposited under the NRRL Accession Number 67646.

Other aspects of the present invention may be accomplished by an *Agaricus bisporus* culture having the same physiological and morphological characteristics as strain J15987, wherein a culture of strain J15987 has been deposited under the NRRL Accession Number 67646. It will be appreciated that the physiological characteristics of the strain will include its performance characteristics as well.

Still further aspects of the present invention may be accomplished by a hybrid mushroom culture of *Agaricus bisporus* having a genotypic fingerprint which has characters at marker loci ITS, p1n150-G3-2, MFPC-1-ELF, AN, AF, and FF, as described in Table VI wherein all of the characters of said fingerprint are present in the genotypic fingerprint of strain J15987. In one or more embodiments, the culture has a genotypic fingerprint having characters at marker loci described in Table V, J15987 column, wherein all of the characters of said fingerprint are present in the genotypic fingerprint of strain J15987.

One or more further aspects of the present invention may be accomplished by a culture, a cell or a culture including the cell, produced by the method(s) above. Thus, one or more embodiments may include a method further including the step of growing the hybrid mushroom culture to produce hybrid mushrooms and parts of mushrooms. Other embodiments may provide for methods wherein the hybrid mushroom culture produced, or the cell, includes a marker profile having characters at marker loci ITS, p1n150-G3-2, MFPC-1-ELF, AN, AF, and FF, wherein all of the characters of said marker profile are also present in the marker profile of J15987. Still other embodiments may provide for methods wherein the hybrid mushroom culture produced, or the cell, includes a marker profile having characters at marker loci described in Table V, J15987 column, wherein all of the characters of said marker profile are also present in the marker profile of J15987

Finally, another aspect of the present invention may be accomplished by a method that uses the hybrid mushroom culture selected from a strain J15987 or Essentially Derived Varieties of strain J15987, a representative culture of the strain having been deposited under NRRL Accession No. 67646. In one embodiment, the method further includes growing a crop of edible mushrooms by carrying out the steps described hereinabove. In another embodiment, the method may include using strain J15987 or essentially derived varieties of strain J15987 in crop rotation to reduce pathogen pressure and pathogen reservoirs in mushroom growing facilities as described hereinabove. In yet another embodiment, the method includes using strain J15987 and Essentially Derived Varieties of strain J15987 to produce offspring as described hereinabove.

DETAILED DESCRIPTION OF THE INVENTION

Initially, in order to provide clear and consistent understanding of the specification and claims, including the scope to be given such terms, the following definitions are provided.

Allele: One or two or more alternative forms of a gene that arise by mutation and are found at the same place on a chromosome; a heritable unit of the genome at a defined locus, ultimately identified by its DNA sequence (or by other means).

Amphithallism: A reproductive syndrome in which heteromixis and intramixis are both active.

Anastomosis: Fusion of two or more hyphae that achieves cytoplasmic continuity.

Basidiomycete: A monophyletic group of fungi producing meiospores on basidia; a member of a corresponding subdivision of Fungi such as the Basidiomycetales or Basidiomycotina.

Basidium: The meiosporangial cell, in which karyogamy and meiosis occur, and upon which the basidiospores are formed.

Bioefficiency: For mushroom crops, the net fresh weight of the harvested crop divided by the dry weight of the compost substrate at the time of spawning, for any given sampled crop area or compost weight.

Breeding: Development of strains, lines or varieties using methods that emphasize sexual mating.

Cap: Pileus; part of the mushroom, the gill-bearing structure.

Cap Roundness: Strictly, a ratio of the maximum distance between the uppermost and lowermost parts of the cap, divided by the maximum distance across the cap, measured on a longitudinally bisected mushroom; typically averaged over many specimens; subjectively, a 'rounded' property of the shape of the cap.

Carrier substrate: A medium having both nutritional and physical properties suitable for achieving both growth and dispersal of a culture; examples are substrates that are formulated for mushroom spawn, casing inoculum, and other inoculum.

Casing layer, casing: A layer of non-nutritive material such as peat or soil that is applied to the upper surface of a mass of colonized compost in order to permit development of the mushroom crop.

Casing inoculum (CI): A formulation of inoculum material incorporating a mushroom culture, typically of a defined heterokaryotic strain, suitable for mixing into the casing layer.

Cloning: Somatic propagation without selection.

Combining ability: The capacity of an individual to transmit superior performance to its offspring. General combining ability is an average performance of an individual in a particular series of matings.

Compatibility: See heterokaryon compatibility, vegetative compatibility, and/or sexual compatibility; incompatibility is the opposite of compatibility.

Culture: The tangible living organism; the organism propagated on various growth media and substrates; a portion of, or the entirety of one physical strain, line, homokaryon or heterokaryon; the sum of all of the parts of the culture, including hyphae, mushrooms, spores, cells, nuclei, mitochondria, cytoplasm, protoplasts, DNA, RNA, proteins, cell membranes and cell walls.

Derivation: Development from a strain; see Essentially Derived Variety (EDV).

Derived lineage group: The set of EDVs derived from a single initial strain or variety.

Descent: Genealogical descent over a limited number (e.g., 10 or fewer) of generations.

Diploid: Having two haploid chromosomal complements within a single nuclear envelope.

Directed mutagenesis: A process of altering the DNA sequence of at least one specific gene locus.

Essential derivation: A process by which an Essentially Derived Variety is obtained from an initial variety or strain or from an EDV of an initial variety or strain; modification of an initial culture using methods including somatic selection, tissue culture selection, selfing including intramictic reproduction via single spores and multiple spores and mating of sibling offspring lines, back-mating to the initial variety, or mutagenesis and/or genetic transformation of the initial variety to produce a distinct culture in which the genotype of the resulting culture is predominantly that of the initial culture.

Essentially Derived Variety (EDV): A congruent, brief, practical definition of an EDV is "a culture derived from an initial culture such that the resulting culture has present at least 75% of the genome or genotype of the initial strain or culture." (Supplemental to the definition of an EDV, it is illustrative to note here that an EDV culture having most or all, but at least 75%, of its genome or genotype present in the genome or genotype of an initial strain or culture may be derived from an initial strain or culture by using a method selected from a group of methods comprising: (a) somatic selection, (b) tissue culture selection, selfing including (c) mating of sibling offspring lines and (d) intramictic reproduction via single or multiple spores, (e) repeated back-mating to the initial line, strain or culture, (f) mutagenesis including induced, directed and targeted mutagenesis (g) genetic transformation (h) a process of single-locus trait conversion, (i) a process of deheterokaryotization, (j) isolation of spontaneous mutants, to produce a culture of an EDV of an initial culture.)

Flesh Thickness: A ratio of the maximum distance between the top of the stem and the uppermost part of the cap, divided by the maximum distance across the cap, measured on a longitudinally bisected mushroom; typically averaged over many specimens; subjectively called 'meatiness'.

Flush: A period of mushroom production within a cropping cycle, separated by intervals of non-production; the term flush encompasses the terms 'break' and 'wave' and can be read as either of those terms.

Fungus: An organism classified as a member of the Kingdom Fungi.

Genealogical relationship: A familial relationship of descent from one or more progenitors, for example that between parents and offspring.

Genetic identity: The genetic information that distinguishes an individual, including representations of said genetic information such as, and including: genotype, genotypic fingerprint, genome sequence, genetic marker profile; "genetically identical"=100% genetic identity, "X % genetically identical"=having X % genetic identity etc.

Genotypic fingerprint: A description of the genotype at a defined set of marker loci; the known genotype.

Gill: Lamella; part of the mushroom, the hymenophore- and basidium-bearing structure.

Haploid: Having only a single complement of nuclear chromosomes; see homokaryon.

Heteroallelic: Having two different alleles at a locus; analogous to heterozygous.

Heteroallelism: Differences between homologous chromosomes in a heterokaryotic genotype; analogous to heterozygosity.

Heterokaryon: As a term of art, this refers to a sexual heterokaryon: a culture which has two complementary (i.e., necessarily heteroallelic at the Mat locus) types of haploid nuclei in a common cytoplasm, and is thus functionally and physiologically analogous to a diploid individual (but cytogenetically represented as N+N rather than 2N), and which is reproductively competent (in the absence of any rare interfering genetic defects at loci other than the Mat locus), and which exhibits vegetative incompatibility reactions with other heterokaryons; also called a strain or stock in the strain development context.

Heterokaryon compatibility: The absence of antagonism observed during physical proximity or contact between two heterokaryons that are not genetically identical; see Heterokaryon Incompatibility.

Heterokaryon incompatibility: The phenomenon of antagonism observed during physical proximity or contact between two heterokaryons that are not genetically identical; a multilocus self/non-self recognition system; i.e., a genetic system that allows one heterokaryon culture to discriminate and recognize another culture as being either self or non-self, that operates in basidiomycete heterokaryons to limit anastomosis (hyphal fusion) and cytoplasmic contact; vegetative incompatibility.

Heterokaryotic: Having the character of a heterokaryon.

Heteromixis: Life cycle involving mating between two different non-sibling haploid individuals or gametes; outbreeding.

Homoallelic: Having not more than one allele at a locus. The equivalent term in a diploid organism is 'homozygous'. Haploid lines are by definition entirely homoallelic at all non-duplicated loci.

Homokaryon: A haploid culture with a single type (or somatic lineage) of haploid nucleus (cytogenetically represented as N), and which is ordinarily reproductively incompetent, and which does not exhibit typical self/non-self incompatibility reactions with heterokaryons, and which may function as a gamete in sexually complementary anastomoses; a 'line' which, as with an inbred plant line, transmits a uniform genotype to offspring; a predominantly homoallelic line that mates well and fruits poorly is a putative homokaryon for strain development purposes; see discussion below.

Homokaryotic: Having the character of a homokaryon; haploid.

Hybrid: Of biparental origin, usually applied to heterokaryotic strains and cultures produced in controlled matings.

Hybridizing: Physical association, for example on a petri dish containing a sterile agar-based nutrient medium, of two cultures, usually homokaryons, in an attempt to achieve anastomosis, plasmogamy, and formation of a sexual heterokaryon (=mating); succeeding in the foregoing.

Hyphae: Threadlike elements of mycelium, composed of cell-like compartments.

Inbreeding: Matings that include sibling-line matings, back-matings to parent lines or strains, and intramixis; reproduction involving parents that are genetically related.

Incompatibility: See heterokaryon incompatibility.

Induced mutagenesis: A non-spontaneous process of altering the DNA sequence of at least one gene locus.

Initial culture: A culture which is used as starting material in a strain development process; more particularly a strain from which an Essentially Derived Variety is obtained.

Inoculum: A culture in a form that permits transmission and propagation of the culture, for example onto new media; specialized commercial types of inoculum include spawn and CI.

Intramixis: A uniparental sexual life cycle involving formation of a complementary 'mated' pair of postmeiotic nuclei within the basidium or individual spore.

Introgressive trait conversion: mating offspring of a hybrid to a parent line or strain such that a desired trait from one strain is introduced into a predominating genetic background of the other parent line or strain.

Lamella: see 'gill'.

Line: A culture used in matings to produce a hybrid strain; ordinarily a homokaryon which is thus homoallelic, otherwise a non-heterokaryotic (non-NSNPP) culture which is highly homoallelic; practically, a functionally homokaryotic and entirely or predominantly homoallelic culture; analogous in plant breeding to an inbred line which is predominantly or entirely homozygous.

Lineage group: see 'derived lineage group'. The set of EDVs derived from a single initial strain or variety.

Locus: A defined contiguous part of the genome, homologous although often varying among different genotypes; plural: loci.

Marker assisted selection: Using linked genetic markers including molecular markers to track trait-determining loci of interest among offspring and through pedigrees.

MAT: The mating-type locus, which determines sexual compatibility and the heterokaryotic state.

Mating: The sexual union of two cultures via anastomosis and plasmogamy; methods of obtaining matings between mushroom cultures are well known in the art.

Mycelium: The vegetative body or thallus of the mushroom organism, comprised of threadlike hyphae.

Mushroom: The reproductive structure of an agaric fungus; an agaric; a cultivated food product of the same name.

Neohaplont: A haploid culture or line obtained by physically deheterokaryotizing (reducing to haploid components) a heterokaryon; a somatically obtained homokaryon.

Offspring: Descendants, for example of a parent heterokaryon, within a single generation; most often used to describe cultures obtained from spores from a mushroom of a strain.

Outbreeding: Mating among unrelated or distantly related individuals.

Parent: An immediate progenitor of an individual; a parent strain is a heterokaryon, a parent line is a homokaryon; a heterokaryon may be the parent of an F1 heterokaryon via an intermediate parent line.

Pedigree-assisted breeding: The use of genealogical information to identify desirable combinations of lines in controlled mating programs.

Phenotype: Observable characteristics of a strain or line as expressed and manifested in an environment.

Plasmogamy: Establishment, via anastomosis, of cytoplasmic continuity leading to the formation of a sexual heterokaryon.

Progenitor: Ancestor, including parent (the direct progenitor).

Selfing: Mating among sibling lines; also intramixis.

Sexual compatibility: A condition among different lines of allelic non-identity at the Mat locus, such that two lines are able to mate to produce a stable and reproductively competent heterokaryon. The opposite condition, sexual incompatibility, occurs when two lines have the same allele at the Mat locus.

Somatic: Of the vegetative mycelium.

Spawn: A mushroom culture, typically a pure culture of a heterokaryon, typically on a sterile substrate which is friable and dispersible particulate matter, in some instances cereal grain; commercial inoculum for compost; reference to spawn includes reference to the culture on a substrate.

Spore: Part of the mushroom, the reproductive propagule.

Stem: Stipe; part of the mushroom, the cap-supporting structure.

Sterile Growth Media: Nutrient media, sterilized by autoclaving or other methods, that support the growth of the organism; examples include agar-based solid nutrient media such as Potato Dextrose Agar (PDA), nutrient broth, and many other materials.

Stipe: see 'stem'.

Strain: A heterokaryon with defined characteristics or a specific identity or ancestry; equivalent to a variety.

Targeted mutagenesis: A process of altering the DNA sequence of at least one specific gene locus.

Tissue culture: A de-differentiated vegetative mycelium obtained from a differentiated tissue of the mushroom.

Trait conversion: A method for the selective introduction of the genetic determinants of one (a single-locus conversion) or more desirable traits into the genetic background of an initial strain while retaining most of the genetic background of the initial strain. See 'Introgressive trait conversion' and 'Transformation'.

Transformation: A process by which the genetic material carried by an individual cell is altered by the incorporation of foreign (exogenous) DNA into its genome; a method of obtaining a trait conversion including a single-locus conversion.

Vegetative compatibility: The absence of the phenomenon of antagonism observed during physical proximity or contact between two heterokaryons that are not genetically identical, determined by a multilocus self/non-self recognition system that operates in basidiomycete heterokaryons to limit anastomosis (hyphal fusion) and cytoplasmic contact; Heterokaryon compatibility; the opposite of Vegetative incompatibility.

Vegetative incompatibility: The phenomenon of antagonism observed during physical proximity or contact between two heterokaryons that are not genetically identical, determined by a multilocus self/non-self recognition system that operates in basidiomycete heterokaryons to limit anastomosis (hyphal fusion) and cytoplasmic contact; Heterokaryon incompatibility.

Virus-breaking: Using multiple incompatible strains, i.e. strains exhibiting heterokaryon incompatibility, successively in a program of planned strain rotation within a mushroom production facility to reduce the transmission of virus from on-site virus reservoirs into newly planted crops.

Yield: The net fresh weight of the harvest crop, normally expressed in pounds per square foot.

Yield pattern: The distribution of yield within each flush and among all flushes; influences size, quality, picking costs, and relative disease pressure on the crop and product.

With respect to the definition of homokaryon above, it is noted that homokaryons and homoallelic lines are subject to technical and practical considerations: A homokaryon in classical terms is a haploid culture which is axiomatically entirely homoallelic. In practical terms, for fungal strain development purposes, the definition is broadened somewhat to accommodate both technical limitations and cytological variation, by treating all predominately homoallelic lines as homokaryons. Technical limitations include the fact that genomes contain duplicated DNA regions including repeated elements such as transposons and may also include large duplications of chromosomal segments due to historical translocation events; such regions may appear not to be homoallelic by most genotyping methods. Two different *A. bisporus* genomes sequenced by the Joint Genome Institute, a U.S. federal facility, differ in estimated length by 4.4%, and in gene numbers by 8.2%, suggesting a considerable amount of DNA duplication or rearrangement within different strains of the species. No presently available genome of *A. bisporus* can completely account for the physical arrangement of such elements and translocations, and so the assembled genome sequences of haploid lines may have regions that appear to be heteroallelic using currently available genotyping methods. Cytologically, a homokaryotic offspring will ordinarily be a spore that receives one haploid, postmeiotic nucleus. However, a spore receiving two third-division nuclei from the basidium will be genetically equivalent to a homokaryon. A spore receiving two second-division 'sister' postmeiotic nuclei will be a functional homokaryon even though some distal 'islands' of heteroallelism may be present due to crossovers during meiosis. Also, a meiosis that has an asymmetrical separation of homologues can produce an aneuploid, functionally homokaryotic spore in which an extra chromosome, producing a region of heteroallelism, is present. All of these cultures are highly homoallelic and all function as homokaryons. Technological limitations make it impractical to distinguish among such cultures, and also to rule out DNA segment duplication as an explanation for limited, isolated regions of the genome sequence assembly that appear to be heteroallelic. Therefore, in the present application, the use of the term 'homoallelic' to characterize a line includes entirely or predominately homoallelic lines, and cultures described in this way are functional homokaryons, are putatively homokaryotic, and are all defined as homokaryons in the present application.

Now, with respect to the invention and as noted hereinabove, the present invention relates to cultures of the hybrid *Agaricus bisporus* strain J15987 and to cultures derived or descended from J15987. Such cultures are used to produce mushrooms and parts of mushrooms. Thus, the present invention further relates to methods of making and using the strain J15987 and Essentially Derived Varieties (EDVs) of the strain J15987.

The morphological and physiological characteristics of strain J15987 in culture on Difco brand PDA medium, which is a standard culture medium, are provided as follows. Strain J15987 growing on PDA medium in an 8.5 cm diameter Petri dish produced a white or light brown-yellow or 'tan' colored irregularly lobate colony with a roughly circular overall outline that increased in diameter by (1.11-1.53) 1.54 (1.55-2.15) mm/day during dynamic equilibrium-state growth between days 10 and 34 after inoculation using a 3.3-3.5 mm diameter circular plug of the culture on PDA as inoculum. Hyphae of the culture on Difco PDA were irregular and about cylindrical, with an internodal measurement of (53–) 61-92 (–105) um, and exhibited a wide range of branching angles from about 10 to 90 degrees off the main hyphal axis. The strain has been increased by transfer of pure inocula into larger volumes of sterile culture media. No variant traits have been observed or are expected in strain J15987.

Hybrid strain J15987 is the product of 7 generations of controlled line matings by Sylvan America, Inc. The original mating was made between line JB 137-s8 and line SWNC. In the sixth generation, line J10102-s69, the subject matter of U.S. Pat. No. 9,648,812, issued May 16, 2017, hereby incorporated by reference, and a descendent of the first hybrid (and of other hybrids produced by Sylvan America, Inc.), was mated with line OWNC to produce the novel hybrid strain J11500, the subject matter of U.S. Pat. No. 9,622,428, issued Apr. 18, 2017, hereby incorporated by reference. In a subsequent generation, homokaryon s-80 from strain J11500 was mated with a second homokaryon (=line), called s-290, from a proprietary experimental breeding stock, to produce the seventh generation hybrid heterokaryon J15987.

Cultures of strain J15987 produce commercially acceptable and desirable crops of white mushrooms. Table I presents yield data as pounds per square foot, in three independent crop tests with internal replication. As shown in Table I, productivity of strain J15987 is comparable to and often greater than the productivity of the A-15 strain, with mean total (2-flush) yields for strain J15987 and the A-15 control strain shown.

TABLE I

Yield of strain J15987 vs A-15, in pounds per square foot, over two flushes, in three tests with two to four replicates for each treatment

| | Total yield | |
| --- | --- | --- |
| Test ID | J15987 | A-15 |
| 16-261 | 4.70 | 4.64 |
| 17-07 | 5.09 | 5.78 |
| 17-159 | 6.15 | 5.72 |

Table I demonstrates that the yield of strain J15987 is comparable to, and can exceed, that of the commercial standard A-15 strain. This is very uncommon for genetically distinct hybrid strains that produce high-quality white mushrooms.

Strain J15987 has an attractive and commercially acceptable appearance, i.e., color and proportions, as can be seen from the data in the following two tables. Mushroom cap surface color is an important element of how the fresh white button mushroom product is perceived, evaluated and valued by all parties including consumers. Color components can be measured objectively by using a Minolta CR-200 Chromameter. Color measurement was measured according to the 'L-a-b' color-space measurement framework. The 'a' measurement component is positively correlated with 'redness'. The smaller the 'a' value, the whiter the mushroom appears and therefore also appears 'fresher' to the human eye. This is an important trait.

Table II reports mean values for color measurement 'a' measured from mushrooms from strains J15987 and A-15 from first and second flush from the same test crop. In addition, p-values from general t-tests of the raw data are displayed. For Table II, medium-sized, closed cap mushrooms were harvested from the first heavy pick day of first flush and of second flush. A total of thirty chromameter readings were taken from individual mushrooms for each strain. Color measurements were taken on the top of the mushroom cap.

TABLE II

Mushroom cap surface redness expressed as 'a' values, for mushrooms of strains J15987 and A-15

| Strain | Flush 1 | Flush 2 |
| --- | --- | --- |
| J15987 | −0.48 | −0.76 |
| A-15 | 0.49 | 0.18 |
| p-value (t-test): | 2.2e-6 | 4.1e-9 |

Data in Table II therefore shows a highly significant difference between J15987 and A-15 for cap redness; J15987 mushroom caps were significantly less red, with a lower 'a' value.

Data in Table III, below, summarize the means of morphometric measurements taken on thirty first-flush mushrooms from each strain. Equal numbers of mushrooms, from the first heavy pick day, of both strains, grown at the same time in the same environment and conditions, were measured. Proportional measures (ratios of two direct measurements) were calculated since absolute dimensions vary widely among mushrooms of any strain and are influenced by cultural factors. (1) 'Cap Diameter' (CD) is defined here as the greatest horizontal distance between two vertical lines tangential to either side of the cap. (2) 'Cap Flesh Thickness' (CFT) is the vertical distance from the top of the lamellae (i.e. gills) adjacent to the stipe, to the surface of the pileus directly above. (3) 'Stem Thickness' (ST) is the greatest horizontal distance across the stem. Two ratios, ST:CD and CFT:CD were compared statistically using a t-test.

TABLE III

Mushroom proportions of strains J15987 and A-15

| Strain | ST | CD | ST:CD | CFT | CFT:CD |
| --- | --- | --- | --- | --- | --- |
| J15987 | 15.16 | 41.70 | 0.36 | 15.35 | 0.37 |
| A-15 | 13.01 | 39.26 | 0.33 | 13.30 | 0.34 |

The p-values obtained from a t-test of the raw data showed that strain J15987 had a significantly thicker stem (p=1.7e-3) and a significantly thicker cap flesh (p=8.8e-4) than the A-15 strain.

Cross-strain incompatibility can also be a useful commercial mushroom trait. Strain J15987 is incompatible with strain A-15, a proxy for the U1 derived lineage group.

A test of compatibility of strain J15987 with the strain A-15, a member of the U1 lineage, was performed in a spawn-mixing experiment; the results are shown in TABLE IV.

TABLE IV

Compatibility of J15987 with A-15 in Spawn-Mixing Experiment

| | Spawn Strain: | | |
| --- | --- | --- | --- |
| | 100% J15987 | 99.5% A-15; 0.5% J15987 | 100% A-15 |
| | Casing Strain: | | |
| | 100% J15987 | 100% A-15 | 100% A-15 |
| Rep 1 | 2.26 lbs. | 0.00 lbs. | 1.76 lbs. |
| Rep 2 | 2.17 lbs. | 0.00 lbs. | 1.74 lbs. |
| Rep 3 | 2.16 lbs. | 0.00 lbs. | 1.73 lbs. |
| Avg. | 2.20 lbs. | 0.00 lbs. | 1.74 lbs. |

Table IV shows that in this test, in the presence of 0.5% (by weight) spawn of strain J15987, mushroom production (i.e., yield) of the A-15 strain was completely prevented, indicating a strong incompatibility reaction between these two strains. This phenomenon tends to prevent anastomosis and viral infection. If fruiting of virus-infected strains in the U1 lineage is also prevented, then virus infection reservoirs of such strains will diminish rapidly in commercial facilities introducing the use of J15987.

The incompatibility phenotype of a strain is known to be routinely transmitted into spores and thus is ordinarily inherited by EDVs derived from spores.

Given that strain J15987 has multiple non-cultivar progenitors, and that considerable genetic diversity exists among strains, the genotypic fingerprint of strain J15987, as expected, shows numerous differences with that of the commercial-standard U1 lineage group. A unique fingerprint allows strain J15987 (and its Essentially Derived Varieties and descendants) to be unambiguously identified. Agronomically, genetic diversity among cultivated strains is a desirable objective because it is well established that genetic monocultures among agricultural crop species can lead to disastrous failures due to particular disease, pest, or environmental pressures. Any otherwise desirable commercial strain with genetic novelty is therefore valuable. Strain J15987 meets those criteria.

For the purpose of this invention, the whole genomic DNA sequence of strain J15987 and of the cultures of its parent lines have been obtained by Sylvan America Inc. using the following method. The homokaryotic parent line cultures were grown in sterile broth growth medium after maceration. After 2-4 weeks, hyphal cells were collected by filtration, were frozen at −80 C, and were lyophilized until dry. Cap tissue was obtained from mushrooms produced by cultures of the heterokaryotic J15987 strain, and was frozen and lyophilized. DNA was extracted from the lyophilized samples using a CTAB protocol followed by RNAse treatment and gel purification. A contractor, SeqWright, prepared DNA libraries from the DNA of each culture, and sequenced the libraries using Illumina MiSeq technology. Assemblies of the reads into genomic sequence using the public-domain reference genome sequence of H97 was performed by the Applicant. Consequently about 93% to about 95% of the entire genotype of strain J15987 and of its parental homokaryons are known to Sylvan America, Inc. with certainty. The total number of markers distinguishing strain J15987 that are known to the assignee is about 325,000. A brief excerpt of the genotype of J15987 and related cultures at numerous sequence-characterized marker loci distributed at intervals along each of the 19 H97 V2.0 reference scaffolds larger than 100 Kb in length is provided in Table V.

TABLE V

| Scaffold | Position of SNP [H97 V2.0 ref. coords.] | H97 | J10102-s69 | J11500 | J11500-s80 | Line s-290 | J15987 |
|---|---|---|---|---|---|---|---|
| 1 | 115817 | CCGAGCGCA | CCGA*A*CGCA | CCGA*r*CGCA | CCGA*A*CGCA | CCGAGCGCA | CCGA*r*CGCA |
| 1 | 349966 | AAGGTGGTT | AAGG*C*GGTT | AAGG*y*GGTT | AAGG*C*GGTT | AAGGTGGTT | AAGG*y*GGTT |
| 1 | 600145 | GTTGGATTA | GTTG*A*ATTA | GTTG*r*ATTA | GTTG*A*ATTA | GTTGGATTA | GTTG*r*ATTA |
| 1 | 850014 | CCTTTTCAC | C*T*TTTT*CG*C | C*y*TTTTC*r*C | C*T*TTTT*CG*C | CCTTTTCAC | C*y*TTTTC*r*C |
| 1 | 1099971 | GTCGACACC | GTCG*G*CACC | GTCG*r*CACC | GTCG*G*CACC | GTCGACACC | GTCG*r*CACC |
| 1 | 1350278 | GGAGAGTCG | GGAG*GT*TCG | GGAG*rk*TCG | GGAG*GT*TCG | GGAGAGTCG | GGAG*rk*TCG |
| 1 | 1599956 | AATAAGCGC | AATA*G*GCGC | AATA*r*GCGC | AATA*G*GCGC | AATAAGCGC | AATA*r*GCGC |
| 1 | 1850032 | CGAGTAATT | CGAG*C*AATT | CGAG*y*AATT | CGAG*C*AATT | CGAGTAATT | CGAG*y*AATT |
| 1 | 2119049 | ACAATCCAA | ACAA*CT*CAA | ACAA*yy*CAA | ACAA*CT*CAA | ACAATCCAA | ACAA*yy*CAA |
| 1 | 2360610 | TTCTACCAC | TTCT*G*CCAC | TTCT*r*CCAC | TTCT*G*CCAC | TTCTACCAC | TTCT*r*CCAC |
| 1 | 2612870 | AATAGGAGT | AATA*A*GAGT | AATA*r*GAGT | AATA*A*GAGT | AATAGGAGT | AATA*r*GAGT |
| 1 | 2804522 | GAAGACGAC | GAAG*GG*GAC | GAAG*rs*GAC | GAAG*GG*GAC | GAAGACGAC | GAAG*rs*GAC |
| 1 | 2858975 | GCCGTTCTT | GCCG*C*TCTT | GCCG*y*TCTT | GCCG*C*TCTT | GCCGTTCTT | GCCG*y*TCTT |
| 1 | 3069801 | CCAAACGCG | CCAA*G*CGCG | CCAA*r*CGCG | CCAA*G*CGCG | CCAAACGCG | CCAA*r*CGCG |
| 1 | 3256057 | TATCTGTTT | TATC*C*GTTT | TATC*y*GTTT | TATC*C*GTTT | TATCTGTTT | TATC*y*GTTT |
| 2 | 101776 | TTACTGCTC | TTACTGCTC | TTACTGCTC | TTACTGCTC | TTAC*C*GCTC | TTAC*y*GCTC |
| 2 | 101820 | ATTAAAGAT | ATTA*CG*GAT | ATTA*m*GAT | ATTAAAGAT | ATTAAAGAT | ATTAAAGAT |
| 2 | 235195 | TTAAATACA | TTAA*GC*ACA | TTAA*ry*ACA | TTAAATACA | TTAAA*C*ACA | TTAAA*y*ACA |
| 2 | 350156 | TCGGGGGTG | TCGG*A*GGTG | TCGG*r*GGTG | TCGGGGGTG | TCGGGGGTG | TCGGGGGTG |
| 2 | 600112 | ATGTATACG | ATGT*G*TACG | ATGT*r*TACG | ATGTATACG | ATGTATACG | ATGTATACG |
| 2 | 850338 | TGGTGCTAA | TGGT*T*CTAA | TGGT*k*CTAA | TGGTGCTAA | TGGTGCTAA | TGGTGCTAA |
| 2 | 1099413 | CCTGACTCA | CCTG*G*CTCA | CCTG*r*CTCA | CCTGACTCA | CCTGACTCA | CCTGACTCA |
| 2 | 1349512 | CTCAGCAGT | CTCA*A*CAGT | CTCA*r*CAGT | CTCAGCAGT | CTCAGCAGT | CTCAGCAGT |
| 2 | 1600085 | CACAATGCC | CACA*T*TGCC | CACA*w*TGCC | CACAATGCC | CACAATGCC | CACAATGCC |
| 2 | 1690101 | ACTTGACAA | ACTTGAC*G*A | ACTTGAC*r*A | ACTTGACAA | A*TT*C*ACAA | A*y*TT*s*ACAA |
| 2 | 1902928 | GATGGATGT | GATG*A*ATGT | GATG*r*ATGT | GATGGATGT | GATGGATGT | GATGGATGT |

TABLE V-continued

| Scaffold | Position of SNP [H97 V2.0 ref. coords.] | Culture: H97 | J10102-s69 | J11500 | J11500-s80 | Line s-290 | J15987 |
|---|---|---|---|---|---|---|---|
| 2 | 1956830 | ATTCCTCAT | ATTC*T*TCAT | ATTC*y*CAT | ATTCCTCAT | ATTC*T*TCAT | ATTC*y*CAT |
| 2 | 2150201 | GTCGTAGGT | GTCG*A*AGGT | GTCG*w*AGGT | GTCGTAGGT | GTCGTAGGT | GTCGTAGGT |
| 2 | 2320631 | GTGACGTTG | GTGAC*A*TTG | GTGAC*r*TTG | GTGACGTTG | GTGA*T*ATTG | GTGA*yr*TTG |
| 2 | 2400354 | CAGAGTCGC | CAGA*T*TCGC | CAGA*k*TCGC | CAGAGTCGC | CAGAGTCGC | CAGAGTCGC |
| 2 | 2650136 | ATAATTCCT | ATAA*A*TCCT | ATAA*w*TCCT | ATAATTCCT | ATAATTCCT | ATAATTCCT |
| 2 | 2903045 | AGAAATAGA | AGAA*G*TAGA | AGAA*r*TAGA | AGAAATAGA | AGAAATAGA | AGAAATAGA |
| 2 | 3047973 | TGACTTCTC | TGACTTCTC | TGACTTCTC | TGACTTCTC | TGAC*C*TCTC | TGAC*y*CTC |
| 2 | 3048019 | GTCCGCTGC | GTCC*A*CTGC | GTCC*r*CTGC | GTCCGCTGC | GTCCGCTGC | GTCCGCTGC |
| 3 | 65650 | GGCGCTTTT | GGCG*G*TTTT | GGCG*s*TTTT | GGCGCTTTT | GGCGCTTTT | GGCGCTTTT |
| 3 | 119281 | TTTATACTC | TTTA*C*ACTC | TTTA*y*ACTC | TTTATACTC | TTTATACTC | TTTATACTC |
| 3 | 249570 | GTATTATGT | GTATTATGT | GTATTATGT | GTATTATGT | GTATTATGT | GTATTATGT |
| 3 | 500000 | GTATACCAA | GTATACCAA | GTATACCAA | GTATACCAA | GTATACCAA | GTATACCAA |
| 3 | 750000 | GTCCGGCCA | GTCCGGCCA | GTCCGGCCA | GTCCGGCCA | GTCCGGCCA | GTCCGGCCA |
| 3 | 1000000 | CACGCGACG | CACGCGACG | CACGCGACG | CACGCGACG | CACGCGACG | CACGCGACG |
| 3 | 1250000 | TTTTTCCGG | TTTTTCCGG | TTTTTCCGG | TTTTTCCGG | TTTTTCCGG | TTTTTCCGG |
| 3 | 1500000 | GTCTGGACA | GTCTGGACA | GTCTGGACA | GTCTGGACA | GTCTGGACA | GTCTGGACA |
| 3 | 1750000 | ACGCCTGAC | ACGCCTGAC | ACGCCTGAC | ACGCCTGAC | ACGCCTGAC | ACGCCTGAC |
| 3 | 2000000 | GTCTCAGGG | GTCTCAGGG | GTCTCAGGG | GTCTCAGGG | GTCTCAGGG | GTCTCAGGG |
| 3 | 2250000 | CGTGGCGAT | CGTGGCGAT | CGTGGCGAT | CGTGGCGAT | CGTGGCGAT | CGTGGCGAT |
| 3 | 2500000 | AATCCTCAC | AATCCTCAC | AATCCTCAC | AATCCTCAC | AATCCTCAC | AATCCTCAC |
| 4 | 100004 | GAGTGATAA | GAGT*A*AT*G*A | GAGT*r*AT*r*A | GAGTGATAA | GAGT*A*AT*G*A | GAGT*r*AT*r*A |
| 4 | 383799 | CAGCCAGAC | CAGC*A*AGAC | CAGC*m*AGAC | CAGCCAGAC | CAGC*A*AGAC | CAGC*m*AGAC |
| 4 | 598147 | GATCGACAG | GATC*A*ACAG | GATC*r*ACAG | GATCGACAG | GATC*A*ACAG | GATC*r*ACAG |
| 4 | 852119 | CGAATATTC | CGAA*C*A*C*TC | CGAA*y*A*y*TC | CGAATATTC | CGAA*C*A*C*TC | CGAA*y*A*y*TC |
| 4 | 1100085 | GATGCCGAA | GATG*A*CGAA | GATG*m*CGAA | GATGCCGAA | GATG*A*CGAA | GATG*m*CGAA |
| 4 | 1350536 | CGAACTCGG | CGAA*AC*CGG | CGAA*my*CGG | CGAACTCGG | CGAA*AC*CGG | CGAA*my*CGG |
| 4 | 1599885 | GATACTTGC | GATA*A*TTGC | GATA*m*TTGC | GATACTTGC | GATA*A*TTGC | GATA*m*TTGC |
| 4 | 1850288 | ATTCGTGTA | ATTC*AC*GTA | ATTC*ry*GTA | ATTCGTGTA | ATTC*AC*GTA | ATTC*ry*GTA |
| 4 | 2100356 | TCAGAGACC | TCAG*G*GACC | TCAG*r*GACC | TCAG*G*GACC | TCAGAGACC | TCAG*r*GACC |
| 4 | 2284257 | TCTGGACTG | TCTG*A*ACTG | TCTG*r*ACTG | TCTG*A*ACTG | TCTGGACTG | TCTG*r*ACTG |
| 5 | 100211 | TCCTTGAAT | TCCT*C*GAAT | TCCT*y*GAAT | TCCT*C*GAAT | TCCTTGAAT | TCCT*y*GAAT |
| 5 | 350872 | GGCGTGCCC | GGCG*C*GCCC | GGCG*y*GCCC | GGCG*C*GCCC | GGCGTGCCC | GGCG*y*GCCC |
| 5 | 599922 | CGTCATTCA | CGTC*G*TTCA | CGTC*r*TTCA | CGTC*G*TTCA | CGTCATTCA | CGTC*r*TTCA |
| 5 | 851262 | TAATTCTCT | TAAT*CG*TCT | TAAT*ys*TCT | TAAT*CG*TCT | TAATTCTCT | TAAT*ys*TCT |
| 5 | 1099776 | ACATTGACA | ACAT*C*GACA | ACAT*y*GACA | ACAT*C*GACA | ACATTGACA | ACAT*y*GACA |
| 5 | 1352539 | TTGTGATCC | TTGT*TG*TCC | TTGT*kr*TCC | TTGT*TG*TCC | TTGTGATCC | TTGT*kr*TCC |
| 5 | 1599904 | AACTTCCTT | AACT*C*CCTT | AACT*y*CCTT | AACT*C*CCTT | AACTTCCTT | AACT*y*CCTT |

TABLE V-continued

| Position of SNP [H97 V2.0 ref. Scaffold coords.] | | Culture: | | | | | |
|---|---|---|---|---|---|---|---|
| | | H97 | J10102-s69 | J11500 | J11500-s80 | Line s-290 | J15987 |
| 5 | 1851458 | AAATAATCC | AAAT*TC*TCC | AAAT*wm*TCC | AAAT*TC*TCC | AAATAATCC | AAAT*wm*TCC |
| 5 | 2100025 | CCCTTAGTC | CCCT*C*AGTC | CCCT*y*AGTC | CCCT*C*AGTC | CCCTTAGTC | CCCT*y*AGTC |
| 5 | 2278878 | GGTCGAAAA | GGTC*A*AAAA | GGTC*r*AAAA | GGTC*A*AAAA | GGTCGAAAA | GGTC*r*AAAA |
| 6 | 106294 | GCCATCTCG | GCCA*C*CTC*A* | GCCA*y*CTC*r* | GCCA*C*CTC*A* | GCCATCTCG | GCCA*y*CTC*r* |
| 6 | 350337 | CATTTGGTT | CATT*C*GGTT | CATT*y*GGTT | CATT*C*GGTT | CATTTGGTT | CATT*y*GGTT |
| 6 | 600047 | GGAGCATTT | GGAG*T*ATTT | GGAG*y*ATTT | GGAG*T*ATTT | GGAGCATTT | GGAG*y*ATTT |
| 6 | 849990 | AGTTCAGGA | AGTT*T*AGGA | AGTT*y*AGGA | AGTT*T*AGGA | AGTTCAGGA | AGTT*y*AGGA |
| 6 | 1098535 | CAAAGATTG | CAAA*A*ATTG | CAAA*r*ATTG | CAAA*A*ATTG | CAAAGATTG | CAAA*r*ATTG |
| 6 | 1349453 | TGTCGGTAG | TGTC*AA*TAG | TGTC*rr*TAG | TGTC*AA*TAG | TGTCGGTAG | TGTC*rr*TAG |
| 6 | 1600000 | AAACCTGGA | AAACCTGGA | AAACCTGGA | AAACCTGGA | AAACCTGGA | AAACCTGGA |
| 6 | 1764645 | AACCGGATT | AACC*A*GATT | AACC*r*GATT | AACC*A*GATT | AACCGGATT | AACC*r*GATT |
| 6 | 2000087 | GATTTGCG | GATT*C*TGCG | GATT*y*TGCG | GATT*C*TGCG | GATTTGCG | GATT*y*TGCG |
| 6 | 2252662 | GGGTTGGTA | GGGT*C*GGTA | GGGT*y*GGTA | GGGT*C*GGTA | GGGTTGGTA | GGGT*y*GGTA |
| 7 | 227441 | ACACATACT | ACAC*G*TACT | ACAC*r*TACT | ACACATACT | ACAC*G*TACT | ACAC*r*TACT |
| 7 | 350044 | ATATTCTTT | ATAT*C*CTTT | ATAT*y*CTTT | ATATTCTTT | ATAT*C*CTTT | ATAT*y*CTTT |
| 7 | 600111 | CAATTATTA | CAAT*C*ATTA | CAAT*y*ATTA | CAATTATTA | CAAT*C*ATTA | CAAT*y*ATTA |
| 7 | 850516 | TGACGCATA | TGAC*A*CATA | TGAC*r*CATA | TGACGCATA | TGAC*A*CATA | TGAC*r*CATA |
| 7 | 1100248 | TCACGGAAG | TCAC*A*GAAG | TCAC*r*GAAG | TCACGGAAG | TCAC*A*GAAG | TCAC*r*GAAG |
| 7 | 1350089 | CTTTTCCCC | CTTT*C*CCCC | CTTT*y*CCCC | CTTTTCCCC | CTTT*C*CCCC | CTTT*y*CCCC |
| 7 | 1605047 | ATACTTGGC | ATAC*G*TG*A*C | ATAC*ktgr*C | ATACTTGGC | ATAC*G*TG*A*C | ATAC*ktgr*C |
| 7 | 1850000 | GAGATACT | GAGATACT | GAGATACT | GAGATACT | GAGATACT | GAGATACT |
| 7 | 1898793 | TCCGCATAA | TCCG*T*AT*G*A | TCCG*y*AT*r*A | TCCGCATAA | TCCG*T*AT*G*A | TCCG*y*AT*r*A |
| 7 | 1991505 | TCTACGGTT | TCTA*AA*GTT | TCTA*mr*GTT | TCTACGGTT | TCTA*AA*GTT | TCTA*mr*GTT |
| 8 | 350000 | ATTGACGCG | ATTGACGCG | ATTGACGCG | ATTGACGCG | ATTGACGCG | ATTGACGCG |
| 8 | 600000 | CATTGACGG | CATTGACGG | CATTGACGG | CATTGACGG | CATTGACGG | CATTGACGG |
| 8 | 850000 | AAATCGCTT | AAATCGCTT | AAATCGCTT | AAATCGCTT | AAATCGCTT | AAATCGCTT |
| 8 | 1100000 | CATACGATC | CATACGATC | CATACGATC | CATACGATC | CATACGATC | CATACGATC |
| 8 | 1350000 | AGCTTAACA | AGCTTAACA | AGCTTAACA | AGCTTAACA | AGCTTAACA | AGCTTAACA |
| 8 | 1600100 | CTGAACCCT | CTGAACCCT | CTGAACCCT | CTGAACCCT | CTGAACCCT | CTGAACCCT |
| 9 | 100105 | CTCAACCGA | CTCA*G*CCGA | CTCA*r*CCGA | CTCAACCGA | CTCAACCGA | CTCAACCGA |
| 9 | 352455 | AGTCCTCCA | AGTC*TC*CCA | AGTC*yy*CCA | AGTCCTCCA | AGTCCTCCA | AGTCCTCCA |
| 9 | 599918 | TATCTCCAC | TATCTCCAC | TATCTCCAC | TATCTCCAC | TATC*G*CCAC | TATC*k*CCAC |
| 9 | 599950 | TGGTATCCC | TGGT*G*TCCC | TGGT*r*TCCC | TGGTATCCC | TGGTATCCC | TGGTATCCC |
| 9 | 798851 | CTTCGATGC | CTTC*A*ATGC | CTTC*r*ATGC | CTTCGATGC | CTTC*A*ATGC | CTTC*r*ATGC |
| 9 | 800528 | TCGACGACC | TCGA*T*GACC | TCGA*y*GACC | TCGACGACC | TCGACGACC | TCGACGACC |
| 9 | 1010845 | GGGTGGTGA | GGGT*A*GTGA | GGGT*r*GTGA | GGGTGGTGA | GGGTGGTGA | GGGTGGTGA |
| 9 | 1050049 | ATCTTTGAT | ATCT*C*TGAT | ATCT*y*TGAT | ATCTTTGAT | ATCT*C*TGAT | ATCT*y*TGAT |

TABLE V-continued

| Scaffold | Position of SNP [H97 V2.0 ref. coords.] | Culture: H97 | J10102-s69 | J11500 | J11500-s80 | Line s-290 | J15987 |
|---|---|---|---|---|---|---|---|
| 9 | 1250269 | CTGTCTTGG | CTGTCTTGG | CTGTCTTGG | CTGTCTTGG | CTGT*T*TTGG | CTGT*Y*TTGG |
| 9 | 1335069 | ATTTGCTTC | ATTT*A*CTTC | ATTT*r*TTC | ATTTGCTTC | ATTTGCTTC | ATTTGCTTC |
| 9 | 1656962 | TATCTACTG | TATC*C*ACTG | TATC*Y*ACTG | TATCTACTG | TATCTACTG | TATCTACTG |
| 10 | 100438 | AATTAATTT | AATT*C*ATTT | AATT*m*ATTT | AATT*C*ATTT | AATTAATTT | AATT*m*ATTT |
| 10 | 299994 | CGCGGGGGC | CGCGGGGGC | CGCGGGGGC | CGCGGGGGC | CGCG*A*GGGC | CGCG*r*GGGC |
| 10 | 352915 | GCGTTCGTG | GCGT*C*CGTG | GCGT*y*CGTG | GCGT*C*CGTG | GCGTTCGTG | GCGT*y*CGTG |
| 10 | 550293 | CGGCTCGGC | CGGCTCGGC | CGGCTCGGC | CGGCTCGGC | CGGC*C*CGGC | CGGC*y*CGGC |
| 10 | 600032 | TTACACTGG | TTAC*G*CTGG | TTAC*r*CTGG | TTAC*G*CTGG | TTACACTGG | TTAC*r*CTGG |
| 10 | 860249 | CCGCAAATT | CCGC*G*AAATT | CCGC*r*AAATT | CCGC*G*AAATT | CCGCAAATT | CCGC*r*AAATT |
| 10 | 1000344 | ATTATGACA | ATTA*C*GACA | ATTA*y*GACA | ATTA*C*GACA | ATTA*C*GACA | ATTA*C*GACA |
| 10 | 1110433 | GGAAGACAA | GGAA*A*CAA | GGAA*r*ACAA | GGAA*A*ACAA | GGAAGACAA | GGAA*r*ACAA |
| 10 | 1303902 | TGATTTACT | TGAT*C*TACT | TGAT*y*TACT | TGAT*C*TACT | TGATTTACT | TGAT*y*TACT |
| 10 | 1330031 | GGATCTGTA | GGAT*T*TGTA | GGAT*y*TGTA | GGAT*T*TGTA | GGAT*T*TGTA | GGAT*T*TGTA |
| 10 | 1490452 | AATCAGATG | AATC*T*GATG | AATC*w*GATG | AATC*T*GATG | AATCAGATG | AATC*w*GATG |
| 11 | 104770 | AATGAGAGG | AATGAGAGG | AATGAGAGG | AATGAGAGG | AATG*G*GAGG | AATG*r*GAGG |
| 11 | 349990 | GACGGCTTC | GACGGCTTC | GACGGCTTC | GACGGCTTC | GACG*A*CTTC | GACG*r*CTTC |
| 11 | 600001 | TGGGCGCGC | TGGGCGCGC | TGGGCGCGC | TGGGCGCGC | TGGG*A*GCGC | TGGG*m*GCGC |
| 11 | 908344 | TAGAAAGAA | TAGAAAGAA | TAGAAAGAA | TAGAAAGAA | TAGA*C*AGAA | TAGA*m*AGAA |
| 11 | 1100296 | TTCTAAAAT | TTCTAAAAT | TTCTAAAAT | TTCTAAAAT | TTCT*G*AAAT | TTCT*r*AAAT |
| 11 | 1239957 | GCTTACTGC | GCTTACTGC | GCTTACTGC | GCTTACTGC | GCTT*G*CTGC | GCTT*r*CTGC |
| 12 | 88001 | ACGACAGAG | ACGACAGAG | ACGACAGAG | ACGACAGAG | ACGA*A*AAG | ACGA*mr*AG |
| 12 | 100000 | CCTTCTAGT | CCTTCTAGT | CCTTCTAGT | CCTTCTAGT | CCTTCTAGT | CCTTCTAGT |
| 12 | 439214 | CACGATGAT | CACGATGAT | CACGATGAT | CACGATGAT | CACG*G*TGAT | CACG*r*TGAT |
| 12 | 700059 | GCTGCCATG | GCTGCCATG | GCTGCCATG | GCTGCCATG | GCTG*T*CATG | GCTG*y*CATG |
| 12 | 1000000 | CGAGGAGGA | CGAGGAGGA | CGAGGAGGA | CGAGGAGGA | CGAGGAGGA | CGAGGAGGA |
| 12 | 1000704 | TTCTGGTGC | TTCTGGTGC | TTCTGGTGC | TTCTGGTGC | TTCT*A*GTGC | TTCT*r*GTGC |
| 13 | 100697 | ACGTCTTTA | ACGT*A*TTTA | ACGT*m*TTTA | ACGT*A*TTTA | ACGT*C*TTA | ACGT*my*TTA |
| 13 | 370946 | AATCTACAA | AATC*C*A*T*AA | AATC*y*A*y*AA | AATC*C*A*T*AA | AATC*C*AC*T*A | AATC*C*A*yw*A |
| 13 | 604345 | CTTCAGCAT | CTTC*C*GCAT | CTT*Cm*GCAT | CTTC*C*GCAT | CTTCAGCAT | CTT*Cm*GCAT |
| 13 | 850249 | GGCTAGTAA | GG*T*GG*T*A | GG*y*T*r*GT*r*A | GG*T*GG*T*A | GG*T*GG*T*A | GG*T*GG*T*A |
| 14 | 113109 | AGGGAAATA | AGGG*G*AATA | AGGG*r*AATA | AGGGAAATA | AGGG*G*AATA | AGGG*r*AATA |
| 14 | 372086 | CGATCCCTT | CGAT*T*C*T*TT | CGAT*y*C*y*TT | CGATCCCTT | CGAT*T*C*T*TT | CGAT*y*C*y*TT |
| 14 | 725684 | ATGAGTTCG | ATGA*A*TT*T*G | ATGA*r*TT*y*G | ATGAGTTCG | ATGA*A*TT*T*G | ATGA*r*TT*y*G |
| 15 | 97145 | TGACGTTTT | TGACGTTTT | TGACGTTTT | TGACGTTTT | TGAC*A*TTTT | TGAC*r*TTTT |
| 15 | 449866 | GAATTTCGG | GAAT*C*TCGG | GAAT*y*TCGG | GAAT*C*TCGG | GAAT*C*TCGG | GAAT*C*TCGG |
| 16 | 208609 | CACATGCAC | CACA*C*GCAC | CACA*y*GCAC | CACA*C*GCAC | CACATGCAC | CACA*y*GCAC |
| 16 | 463539 | TCGTTCACC | TCGT*C*CACC | TCGT*y*CACC | TCGT*C*CACC | TCGTTCACC | TCGT*y*CACC |

TABLE V-continued

| Scaffold | Position of SNP [H97 V2.0 ref. coords.] | Culture: | | | | | |
|---|---|---|---|---|---|---|---|
| | | H97 | J10102-s69 | J11500 | J11500-s80 | Line s-290 | J15987 |
| 17 | 119990 | AAAATTGCG | AAAATTGCG | AAAATTGCG | AAAATTGCG | AAAACTGCG | AAAAYTGCG |
| 17 | 338415 | TGAGAAGCC | TGAGGAGCC | TGAGRAGCC | TGAGGAGCC | TGAGAAGCC | TGAGRAGCC |
| 17 | 449833 | ATCAGACAA | ATCAAACTA | ATCARACWA | ATCAAACTA | ATCAAACTA | ATCAAACTA |
| 18 | 101884 | ATTACGGAC | ATTATGGAC | ATTAYGGAC | ATTACGGAC | ATTATGGAC | ATTAYGGAC |
| 19 | 98377 | GCTATTGGG | GCTACTGGG | GCTAYTGGG | GCTATTGGG | GCTACTGGG | GCTAYTGGG |

Table V presents a 'fingerprint' excerpted from the SNP (Single Nucleotide Polymorphism) marker genotype of the entire genome sequences of hybrid strain J15987 and of related cultures. The IUPAC nucleotide and ambiguity codes are used to represent the observed 9-base DNA marker sequences reported above, each of which represents a genotypic marker locus. The identity of each marker locus is specified by the scaffold and SNP position information derived from the H97 V2.0 reference genome sequence published by the U.S. Department of Energy Joint Genome Institute (Morin et al. 2012). It is evident that a composite relationship of the heteroallelic genotype of strain J15987 exists with respect to the homoallelic genotypes of its two parental lines, namely line J11500-s80 and line s-290.

A brief description of the genotype of strain J15987 at further six unlinked marker loci is provided below. Because the J15987 heterokaryon incorporates two sets of chromosomes, there are two allelic copies (two characters or elements of the genotype) at each marker locus. The brief genotype excerpt provided below therefore consists of 12 characters or elements. The brief genotype was prepared by the assignee of record using targeted Polymerase Chain Reactions to amplify genomic regions bracketing the defined markers from each of the culture DNAs. Any suitable PCR primers that bracket the defined marker regions may be used for this purpose; methods of designing suitable primers are well known in the art. From the amplified PCR product, DNA was sequenced by a contractor, Eurofins, using methods of their choice, and the genotypes were determined by direct inspection of these sequences in comparison to Sylvan America's database of reference marker/allele sequences. In most cases the sequence was further confirmed by direct inspection of the corresponding whole genome sequence for that culture.

Description of the p1n150-G3-2 Marker:

The 5' end of this marker segment begins at position 1 with the first "T" in the sequence TCCCAAGT, corresponding to H97 JGI V2.0 Scaffold 1 position 868615 (Morin et al. 2012) and extending in a reverse orientation (relative to the scaffold orientation) for ca. 600 nt in most alleles; an insertion in the DNA of allele 1T has produced a longer segment. At present, 9 alleles incorporating at least 30 polymorphic positions have been documented from diverse strains in Sylvan America's breeding collection.

Alleles present in the J15987 pedigree over three generations are alleles 1T and 2, characterized as follows (using the format: nucleotide base character @ alignment position, based on alignment of alleles 2, 3, and 4, and the alignable portions of allele 1T):

Allele 1T: 'C' @ 193; insertion of Abr1 transposon of 320 nt @ 206^207; 'T' @ 327; 'C' @ 374; 'G' @ 378; 'G' @ 422; 'C' @ 431; 'G' @ 472; etc.

Allele 2: no Abr1 insertion; 'C' @ 193; 'C' @ 327, 'C' @ 374; 'C' @ 378; 'G' @ 422; 'T' @ 431; 'G' @ 472; etc.\

Because of linkage to the MAT locus, which is obligatively heteroallelic in fertile heterokaryons, genotypes of all known and expected heterokaryons at p1n150-G3-2 are also heteroallelic.

The genotype of the J15987 heterokaryon at the p1n150-G3-2 marker locus is '1T/2' (heteroallelic), designating the presence of alleles 1T and 2. Allele 1T was contributed by line s-290. Allele 2 was transmitted from the J11500-s80 line. The '1T/2' genotype distinguishes J15987 from many other heterokaryons, although not from the U1 strain family.

Description of the ITS (=ITS 1+2 Region) Marker:

The ITS segment is part of the nuclear rDNA region which is located on chromosome 9 (Scaffold 10 in JGI H97 V2.0). The rDNA is a cassette that is tandemly repeated up to an estimated 100 times in the haploid genome of A. bisporus. Therefore, there is no single precise placement of this sequence in the assembled H97 genome, and in fact it is difficult or impossible to precisely assemble the sequence over all the tandem repeats. Three cassette copies were included on scaffold 10 of the H97 JGI V2.0 assembly, beginning at position 1612110; a partial copy is also assembled into scaffold 29 (Morin et al. 2012). The 5' end of this marker segment begins at position 1 with the first "G" in the sequence GGAAGGAT and extending in a forward orientation (relative to the scaffold orientation) for ca. 703-704 nt in most alleles. At present, more than 9 alleles incorporating at least 11 polymorphic positions have been documented from diverse strains in Sylvan America's breeding collection.

Alleles present in the J15987 immediate pedigree are alleles I1, I2, and I4, characterized as follows (using the format: nucleotide base character @ alignment position, based on alignment of 9 alleles).

Allele I1: 'C' @ 52; 'T' @ 461; 'T' @ 522; 'T' @ 563; etc.

Allele I2: 'T' @ 52; 'T' @ 461; 'T' @ 522; 'T' @ 563; etc.

Allele I4: 'C' @ 52; 'A' @ 461; 'C' @ 522; 'C' @ 563; etc.

The line J11500-s80 homokaryon has an 'I4' genotype.

The line s-290 homokaryon has an 'I2' genotype.

The genotype of the J15987 heterokaryon at the ITS marker locus is 'I2/I4' (heteroallelic), designating the presence of alleles I2 and I4. This distinguishes J15987 from the U1 strain family, which has an 'I1/I2' genotype, and from many other strains.

Description of the MFPC-1-ELF Marker:

The 5' end of this marker segment begins at position 1 with the first "G" in the sequence GGGAGGGT, corresponding to H97 JGI V2.0 Scaffold 8 position 829770 (Morin et al. 2012) and extending in a forward orientation (relative to the scaffold orientation) for ca. 860 nt in most alleles. At present, at least 7 alleles incorporating at least 40 polymorphic positions have been documented from diverse strains in Sylvan America's breeding collection.

Allele E1: 'A' @ 77; 'A' @ 232; 'A' @ 309; 'T' @ 334; 'A' @ 390; 'A' @ 400; 'T' @ 446, 'A' @ 481; etc.

Allele E2: 'G' @ 77; 'A' @ 232; 'G' @ 309; 'T' @ 334; 'G' @ 390; 'G' @ 400; 'C' @ 446; 'G' @ 481; etc.

The homokaryon stocks (H97, J10102-s69, line J11500-s80 and line s-290 all have the 'E1' allele, which is correlated with white cap color.

The Sylvan hybrid heterokaryon stocks J11500 and J15987 are both 'E1/E1'. This homoallelic genotype distinguishes J15987 from the U1-derived commercial cultivar lineage, which has an 'E1/E2' genotype.

Description of the AN Marker:

The 5' end of this marker segment begins at position 1 with the first "G" in the sequence GGGTTTGT, corresponding to H97 JGI V2.0 Scaffold 9 position 1701712 (Morin et al. 2012) and extending in a forward orientation (relative to the scaffold orientation) for ca. 1660 (in the H97 genome) to 1700 nt (in alignment space) in known alleles; several insertions/deletions have created length polymorphisms which, in addition to point mutations of individual nucleotides, characterize the alleles. At present, 5 alleles incorporating more than 70 polymorphic positions have been documented from diverse strains in Sylvan America's breeding collection.

Alleles present in the J15987 immediate pedigree are alleles N1 and N5, characterized in part as follows (using the format: nucleotide base character @ alignment position, based on alignment of alleles N1 through N5):

Allele N1: 'G' @ 640; [deletion] @ 844-846; 'T' @ 882; 'A' @ 994, etc.

Allele N2: 'A' @ 640; [deletion] @ 844-846; 'T' @ 882; 'A' @ 994, etc.

Allele N5: 'A' @ 640; 'ACG' @ 844-846; 'C' @ 882; 'G' @ 994, etc.

The line J11500-s80 homokaryon has an 'N1' genotype.

The line s-290 homokaryon has an 'N1' genotype.

The 'N1/N1' genotype of strain J15987 at the AN marker locus distinguishes J15987 from commercial strains U1 and derivatives including A-15, which have an 'N1/N2' genotype, and also from many other strains.

Description of the AS Marker:

The 5' end of this marker segment begins at position 1 with the first "G" in the sequence GG(T/N)GTGAT, corresponding to H97 JGI V2.0 Scaffold 4 position 752867 (Morin et al. 2012) and extending in a forward orientation (relative to the scaffold orientation) for ca. 1620 (in the H97 genome) to 1693 nt (in alignment space) in known alleles; several insertions/deletions have created length polymorphisms which, in addition to point mutations of individual nucleotides, characterize the alleles. At present, 7 alleles incorporating more than 80 polymorphic positions have been documented from diverse strains in Sylvan America's breeding collection.

Alleles present in the J15987 immediate pedigree are alleles SC and SD, characterized in part as follows (using the format: nucleotide base character @ alignment position, based on alignment of alleles SA through SG):

Allele SC: 'T' @ 28; 'GATATC' @ 258-263; 'G' @ 275; [insertion]+'TTTCTCAGC'+[insertion] @ 309-249; 'C' @ 404, etc.

Allele SD: 'C' @ 28; [deletion] @ 258-263; 'T' @ 275; [deletion] @ 309-249; 'T' @ 404, etc.

The line J11500-s80 homokaryon has the 'SD' genotype.

The line s-290 homokaryon has the 'SC' genotype.

The J15987 heterokaryon has the 'SC/SD' genotype.

The 'SC/SD' genotype at the AS marker locus is also shared by commercial strains U1 and A-15. This element of the genotype fingerprint distinguishes J15987 from among many strains other than the U1 strain family.

Description of the FF Marker:

The 5' end of this marker segment begins at position 1 with the first "T" in the sequence TTCGGGTG, corresponding to H97 JGI V2.0 Scaffold 12 position 281999 (Morin et al. 2012) and extending in a forward orientation (relative to the scaffold orientation) for ca. 570 nt in most alleles. At present, 7 alleles incorporating at least 20 polymorphic positions have been documented from diverse strains in Sylvan America's breeding collection.

Alleles present in the J15987 immediate pedigree are alleles FF1 and FF2, characterized as follows (using the format: nucleotide base character @ alignment position, based on alignment of alleles 1 and 2):

Allele FF1: 'CCG' @ 48-50

Allele FF2: 'TTC' @ 48-50

The line J11500-s80 homokaryon has an 'FF1' genotype.

The line s-290 homokaryon has an 'FF2' genotype.

The genotype of the J15987 heterokaryon at the FF marker locus is 'FF1/FF2' (heteroallelic). Commercial strains U1 and A15 also share the 'FF1/FF2' genotype.

The genotype data for the six additional marker loci in standard use as discussed above are provided in Table VI.

TABLE VI

Genotypes of relevant cultures at six standard marker loci

| Strain | p1n150/Mat | ITS | MFPC-ELF | AN | AS | FF |
| --- | --- | --- | --- | --- | --- | --- |
| U1 | 1T/2 | I1/I2 | E1/E2 | N1/N2 | SC/SD | FF1/FF2 |
| H97 | 1T | I1 | E1 | N1 | SD | FF1 |
| J10102-s69 | 2 | I4 | E1 | N5 | SC | FF1 |
| J11500 | 1T/2 | I1/I4 | E1/E1 | N1/N5 | SC/CD | FF1/FF1 |
| J11500-s80 | 2 | I4 | E1 | N1 | SD | FF1 |
| Line s-290 | 1T | I2 | E1 | N1 | SC | FF2 |
| J15987 | 1T/2 | I2/I4 | E1/E1 | N1/N1 | SC/SD | FF1/FF2 |

One use of the culture of strain J15987 is the production of crops of edible mushrooms for sale. Another use is for the improvement of facility hygiene via strain rotation and a 'virus-breaking' effect. A third use is to incorporate the genetic material of strain J15987 into offspring and derived or descended cultures including dormant and germinating spores and protoplasts. Additional uses also exist as noted above.

Hybridization of *Agaricus bisporus* cultures of the invention may be accomplished by allowing two different cultures, one of which is a genetic line present in a spore of strain J15987, to grow together in close proximity, preferably on sterile media, until anastomosis (i.e., hyphal or cell fusion) occurs. In a successful mating, the resultant fusion culture is a first-generation outbred hybrid culture incorporating a genetic line present in a mushroom spore which is one part of one embodiment of the present invention. Protoplasts derived from basidia or other parts of the organism are another part of the J15987 mushroom that may be used to transmit genetic material of strain J15987 into new cultures.

Methods for obtaining, manipulating, and mating cultures of the present invention, for producing offspring, inoculum, products, and crops of the current invention, for using a strain rotation program to improve mushroom farm hygiene, and for obtaining the genotypic fingerprint of mushroom cultures, are described hereinabove and are also well known to practitioners of the art.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. A hybrid mushroom culture of *Agaricus bisporus* comprising: a culture designated as strain J15987, a representative culture of the strain having been deposited under NRRL Accession No. 67646.

2. An Essentially Derived Variety of the hybrid mushroom culture designated as strain J15987 of claim 1, wherein said Essentially Derived Variety is a culture of a strain derived from an initial culture of strain J15987, wherein a culture of the strain has been deposited under NRRL Accession No. 67646, such that at least 75% of its genome or genotype is present in the genome or genotype of the initial culture of strain J15987.

* * * * *